(12) United States Patent
Bradley

(10) Patent No.: US 9,037,261 B2
(45) Date of Patent: May 19, 2015

(54) METHOD FOR IMPROVING FAR-FIELD ACTIVATION IN PERIPHERAL FIELD NERVE STIMULATION

(71) Applicant: BOSTON SCIENTIFIC NEUROMODULATION CORPORATION, Valencia, CA (US)

(72) Inventor: Kerry Bradley, Glendale, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 0 days.

(21) Appl. No.: 14/189,660

(22) Filed: Feb. 25, 2014

(65) Prior Publication Data

US 2014/0180350 A1    Jun. 26, 2014

Related U.S. Application Data

(63) Continuation of application No. 13/529,928, filed on Jun. 21, 2012, now Pat. No. 8,700,180.

(60) Provisional application No. 61/500,566, filed on Jun. 23, 2011.

(51) Int. Cl.
*A61N 1/05*     (2006.01)
*A61N 1/36*     (2006.01)

(52) U.S. Cl.
CPC .......... *A61N 1/36071* (2013.01); *A61N 1/0551* (2013.01); *A61N 1/3605* (2013.01)

(58) Field of Classification Search
USPC .................. 607/1–2, 115–116, 118
See application file for complete search history.

(56) References Cited

U.S. PATENT DOCUMENTS

| | | | |
|---|---|---|---|
| 6,516,227 B1 | 2/2003 | Meadows et al. | |
| 6,895,280 B2 | 5/2005 | Meadows et al. | |
| 7,539,538 B2 | 5/2009 | Parramon et al. | |
| 7,742,810 B2 | 6/2010 | Moffitt et al. | |
| 2002/0055779 A1* | 5/2002 | Andrews | 623/11.11 |
| 2003/0139781 A1 | 7/2003 | Bradley et al. | |
| 2003/0236558 A1* | 12/2003 | Whitehurst et al. | 607/45 |
| 2004/0015205 A1 | 1/2004 | Whitehurst et al. | |
| 2005/0267546 A1 | 12/2005 | Parramon et al. | |
| 2010/0016929 A1* | 1/2010 | Prochazka | 607/72 |
| 2010/0324630 A1 | 12/2010 | Lee et al. | |

\* cited by examiner

*Primary Examiner* — Deborah Malamud
(74) *Attorney, Agent, or Firm* — Faegre Baker Daniels LLP

(57) ABSTRACT

A method of providing therapy to a patient having a disorder using an electrode located adjacent a peripheral target neural region. The method comprises conveying electrical stimulation energy from the electrode that stimulates a first set of nerve endings in the peripheral target neural region. The method further comprises increasing an activation threshold of a second set of nerve endings in the peripheral target neural region, thereby rendering the second set of nerve endings less excitable to the electrical stimulation energy. The first set of nerve endings are relatively far from the electrode and the second set of nerve endings are relatively near the electrode.

19 Claims, 3 Drawing Sheets

METHOD FOR IMPROVING FAR-FIELD ACTIVATION IN PERIPHERAL FIELD NERVE STIMULATION

RELATED APPLICATION DATA

The present application is a continuation of U.S. patent application Ser. No. 13/529,928, filed Jun. 21, 2012, now issued as U.S. Pat. No. 8,700,180, which claims the benefit under 35 U.S.C. §119 to U.S. provisional patent application Ser. No. 61/500,566 filed Jun. 23, 2011, which applications are incorporated herein by reference.

FIELD OF THE INVENTION

The present invention relates to tissue stimulation systems, and more particularly, to a system and method for performing peripheral nerve field stimulation.

BACKGROUND OF THE INVENTION

Implantable neurostimulation systems have proven therapeutic in a wide variety of diseases and disorders. In recent investigations, Peripheral Stimulation (PS) (i.e., stimulation of nerve tissue outside of the spinal cord and brain), which includes Peripheral Nerve Field Stimulation (PNFS) techniques that stimulate nerve tissue (and in particular, nerve endings, defined to be the distal ends of the neurons which are made up of the receptors (mechanical, chemical, thermal, non-specific, etc) and the axonal regions that connect the receptors to the main axon traversing to the central nervous system, these axonal regions being typically several mm in length) directly at or near the symptomatic site of the disease or disorder (e.g., at the source of pain), and Peripheral Nerve Stimulation (PNS) techniques that directly stimulate bundles of peripheral nerves (in particular, neural axons) that may not necessarily be at the symptomatic site of the disease or disorder, has demonstrated efficacy in the treatment of chronic pain syndromes (e.g., painful peripheral neuropathy (PN), post-herpetic neuralgia (PHN), fibromyalgia syndrome (FMS), failed back surgery syndrome (FBSS), Arachnoiditis, occipital neuralgia, peripheral pelvic pain, cardiac pain, etc.) and incontinence, and a number of additional applications are currently under investigation.

An implantable neurostimulation system, whether used in the context of PS or another stimulation application, typically includes one or more electrode carrying stimulation leads, which are implanted at the desired stimulation site. In PS, the stimulation lead(s) are implanted in the subcutaneous tissues of a peripheral region, such as the lower back region, cervical region, arm, or leg. With respect to PNS, the electrode or electrodes are placed directly on or in close proximity to a particular nerve, whereas with respect to PNFS, the electrode or electrodes are placed in a painful area without respect to a particular nerve's location). The implantable neurostimulation system further includes a neurostimulator (e.g., an implantable pulse generator (IPG)) implanted within a tissue pocket remotely from the stimulation site, but coupled to the stimulation lead(s). Thus, electrical pulses can be delivered from the neurostimulator to the stimulation lead(s) to stimulate or activate a volume of neural tissue. In particular, electrical energy conveyed between at least one cathodic electrode and at least one anodic electrodes creates an electrical field, which when strong enough, depolarizes (or "stimulates") the neurons beyond a threshold level, thereby inducing the firing of action potentials (APs) that propagate along the neural fibers.

Stimulation energy may be delivered to the electrodes during and after the lead placement process in order to verify that the electrodes are stimulating the target neural elements and to formulate the most effective stimulation regimen. The regimen will dictate which of the electrodes are sourcing current pulses (anodes) and which of the electrodes are sinking current pulses (cathodes) at any given time, as well as the magnitude, duration, and rate of the current pulses. The stimulation regimen will typically be one that provides stimulation energy to all of the target tissue that must be stimulated in order to provide the therapeutic benefit, yet minimizes the volume of non-target tissue that is stimulated. In the case of PS, such a therapeutic benefit is accompanied by "paresthesia," i.e., a tingling sensation that is effected by the electrical stimuli applied through the electrodes.

With respect to PNFS, it is desirable that the entire target tissue (i.e., the nerve tissue responsible for the pain) be stimulated. However, it is generally not practical to cover the entire target tissue with stimulating electrodes. Thus, since the target tissue will typically extend beyond the locations of the electrode or electrodes, the amplitude of electrical stimulation energy conveyed by these electrode(s) must be increased in order to expand the electrical stimulation field to the outer reaches of the target tissue; that is, to provide far field stimulation at neural locations that are far from the activated electrode(s). This results in wider regions of paresthesia sensation, which may relate to broader regions of pain relief. Oftentimes, because the amplitude of the electrical stimulation energy must be increased to stimulate neurons in the far field, this may result in a painful "pinch" sensation in the tissue (e.g., by stimulating A-delta fibers) adjacent the stimulation electrode(s). Thus, the stimulation coverage may be limited by the painful sensations experienced by the patient at the stimulation electrode(s).

There, thus, remains a need for an improved technique to perform PNFS in order to treat the entirety of the pain region while avoiding or minimize the occurrence of pain in the tissue adjacent the stimulating electrodes that may result from the stimulation itself.

SUMMARY OF THE INVENTION

In accordance with the present inventions, a method of providing therapy to a patient having a disorder (e.g., chronic pain) is provided. The method uses an electrode located adjacent a peripheral target neural region comprising nerve endings. The method comprises conveying electrical stimulation energy from the electrode that stimulates a first set of nerve endings in the peripheral target neural region. The electrical stimulation energy may be conveyed, e.g., in a monopolar manner (where one of the delivery electrodes is a large, distant contact, often the case containing the bulk of the stimulating electronics) or a bipolar manner. The method further comprises increasing an activation threshold of a second set of nerve endings in the peripheral target neural region, thereby rendering the second set of nerve endings less excitable to the electrical stimulation energy. The first set of nerve endings are relatively far from the electrode, and the second set of nerve endings are relatively near the electrode. Increasing the activation threshold of the second set of nerve endings may result in preventing stimulation of the second set of nerve endings.

In one method, conveying the electrical stimulation energy may comprise conveying at least one stimulation pulse, and increasing the activation threshold of the second set of nerve endings may be performed by conveying at least one electrical conditioning pulse (e.g., a depolarizing conditioning pulse or a hyperpolarizing conditioning pulse having a relatively short pulse duration (e.g., less than 200 µs)) to the second set of nerve endings. The conditioning pulse(s) may be conveyed from the electrode and may respectively precede the stimulation pulse(s).

In another method, increasing the activation threshold of the second set of nerve endings is performed by conveying high frequency electrical blocking energy (e.g., sinusoidal energy at a frequency of at least 2.2 KHz) to the second set of nerve endings. The high frequency electrical blocking energy may be the same as the electrical stimulation energy conveyed from the electrode or may be different from the electrical stimulation energy, in which case, the conveyance of the high frequency electrical blocking energy may be ceased during a plurality of periods, and the electrical stimulation energy in the form of a plurality of stimulation pulses may be respectively conveyed only during the plurality of periods. In this case, the high frequency electrical blocking energy may be at least 2.2 KHz, the plurality of stimulation pulses may be conveyed at a frequency in the range of 20-100 Hz, and the energy in the plurality of stimulation pulses may be greater than the high frequency electrical blocking energy.

In yet another method, increasing the activation threshold of the second set of nerve endings is performed by conveying pulsed electrical energy prior to conveying the electrical stimulation energy, such that the second set of nerve endings accommodates to the conveyed electrical stimulation energy. In this case, the pulsed electrical energy has an amplitude that is less than the electrical stimulation energy. In still another method, the activation threshold of the second set of nerve endings is performed by applying a neuronal inhibitory pharmacological agent to the second set of nerve endings prior to conveying the electrical stimulation energy from the electrode. In still another method, the activation threshold of the second set of nerve endings is performed by ablating (complete or incomplete) the second set of nerve endings.

Other and further aspects and features of the invention will be evident from reading the following detailed description of the preferred embodiments, which are intended to illustrate, not limit, the invention.

BRIEF DESCRIPTION OF THE DRAWINGS

The drawings illustrate the design and utility of preferred embodiments of the present invention, in which similar elements are referred to by common reference numerals. In order to better appreciate how the above-recited and other advantages and objects of the present inventions are obtained, a more particular description of the present inventions briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which.

DETAILED DESCRIPTION OF THE EMBODIMENTS

Figure 1:
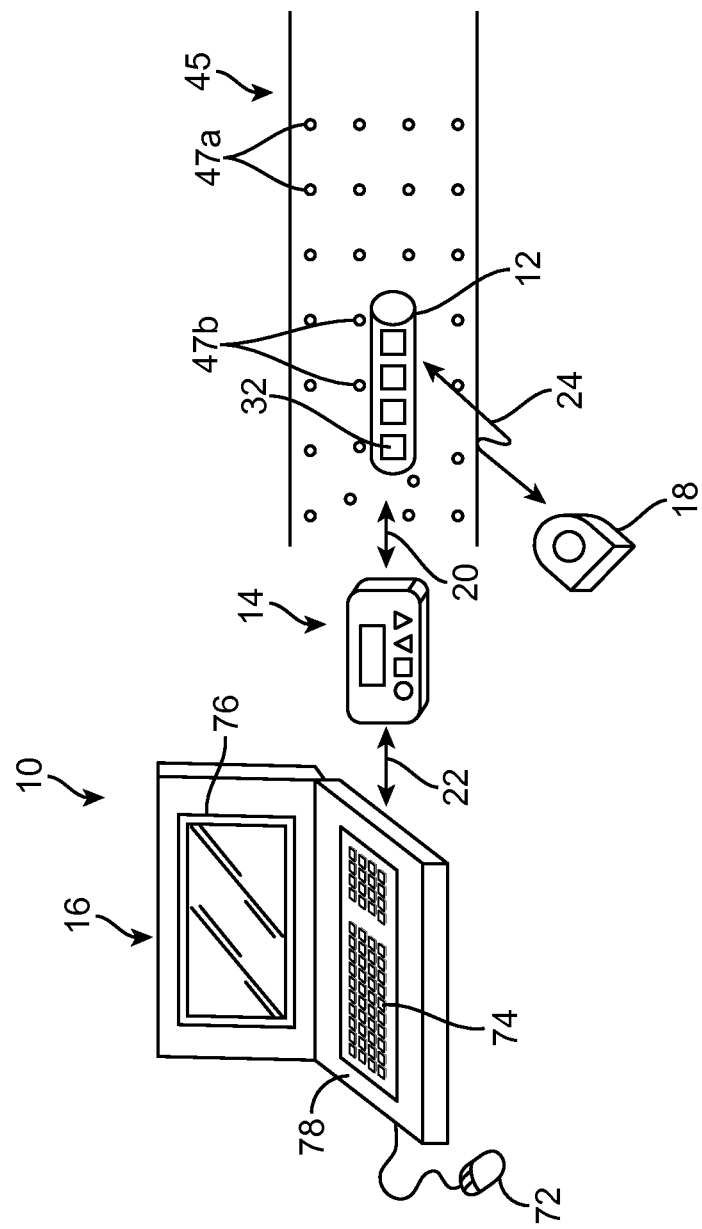
FIG. 1 is plan view of one embodiment of a peripheral tissue stimulation system arranged in accordance with the present inventions.

Turning first to FIG. 1, an exemplary neurostimulation system 10 is used to selectively perform Peripheral Nerve Field Stimulation (PNFS). The system 10 generally includes a neurostimulator in the form of a microstimulator 12, external control devices, and in particular a handheld remote controller (RC) 14 and a clinician's programmer (CP) 16, and an external charger 18.

The microstimulator 12 includes pulse generation circuitry that delivers electrical stimulation energy in the form of a pulsed electrical waveform (i.e., a temporal series of electrical pulses) to tissue in which the microstimulator 12 is implanted in accordance with a set of stimulation parameters. As shown in FIG. 1, the microstimulator 12 is subcutaneously implanted within a peripheral target region 45 (e.g., an arm, leg, lower back, neck, etc.) of a patient using suitable means, such as a needle. As there shown, the peripheral target region 45 includes nerve endings 47 that provide sensory information local to the peripheral region 45. A first set of nerve endings 47a are located a relatively far distance from the implanted microstimulator 12 and a second set of nerve endings 47b are located a relatively short distance from the implanted microstimulator 12.

The RC 14 may be used to telemetrically control the microstimulator 12 via a bi-directional RF communications link 20. Such control allows the microstimulator 12 to be turned on or off and to be programmed with different stimulation parameters. The microstimulator 12 may also be operated to modify the programmed stimulation parameters to actively control the characteristics of the electrical stimulation energy output by the microstimulator 12.

The CP 16 provides clinician detailed stimulation parameters for programming the microstimulator 12 in the operating room and in follow-up sessions. The CP 16 may perform this function by indirectly communicating with the microstimulator 12 through the RC 14 via an IR communications link 22. Alternatively, the CP 16 may directly communicate with the microstimulator 12 via an RF communications link (not shown). The clinician detailed stimulation parameters provided by the CP 16 are also used to program the RC 14, so that the stimulation parameters can be subsequently modified by operation of the RC 14 in a stand-alone mode (i.e., without the assistance of the CP 16).

The external charger 18 is a portable device used to transcutaneously charge the microstimulator 12 via an inductive link 24. For purposes of brevity, the details of the external charger 18 will not be described herein. Once the microstimulator 12 has been programmed, and its power source has been charged by the external charger 18 or otherwise replenished, the microstimulator 12 may function as programmed without the RC 14 or CP 16 being present.

For purposes of brevity, the details of the RC 14, CP 16, and external charger 18 will not be described herein. Details of exemplary embodiments of these devices are disclosed in U.S. Pat. No. 6,895,280, which is expressly incorporated herein by reference.

Figure 2:
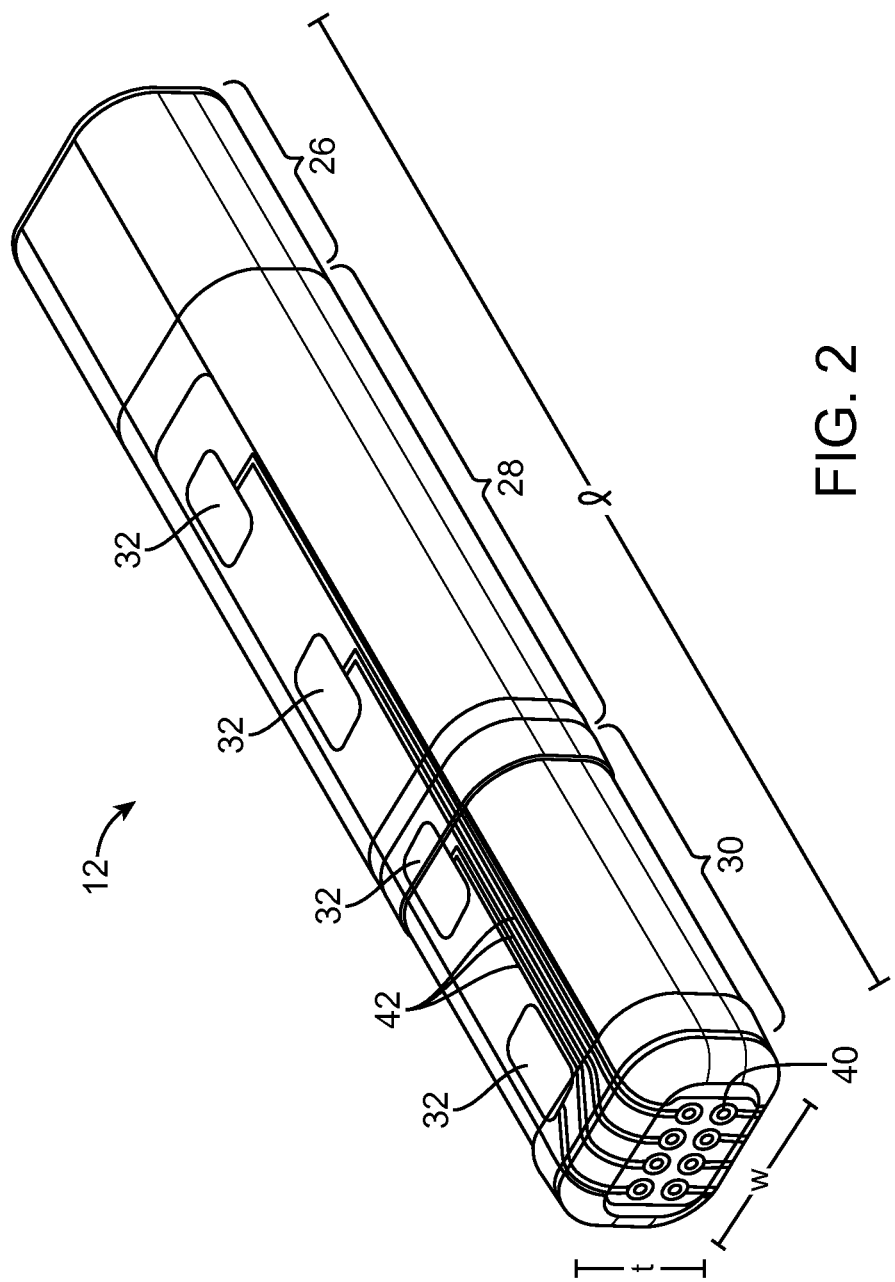
FIG. 2 is a perspective view of a microstimulator used in the peripheral stimulation system of FIG. 1.
Figure 3:
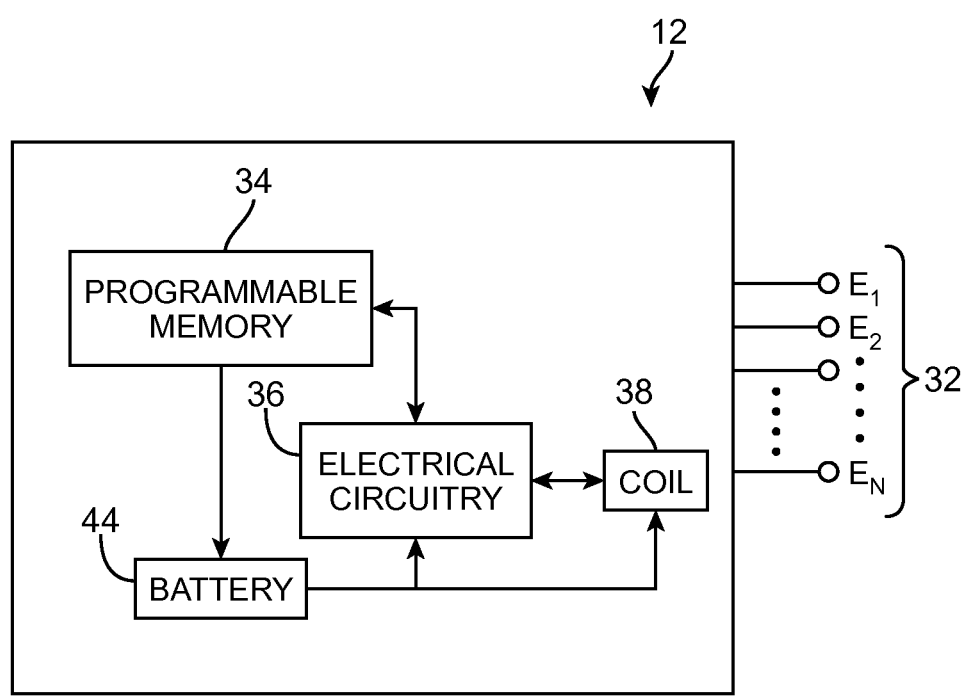
FIG. 3 is a block diagram of the internal components of the microstimulator of FIG. 2.

Turning to FIGS. 2 and 3, the microstimulator 12 is designed to stimulate tissue that is local to its implantation site. Preferably, the microstimulator 12 is small enough to be implanted almost anywhere in the human body for treatment of a wide variety of diseases and disorders. For example, the microstimulator 12 may have a length l in the range of 26-30 mm, a width w in the range of 6.5-8 mm, and a thickness t in the range of 3.5-5 mm. The microstimulator 12 is generally rectangular, although it should be understood that the microstimulator 12 may alternatively be cylindrical, elongated oval, square, or any other suitable shape.

To this end, the microstimulator 12 comprises a circuit module 26, an energy storage module 28, a feed-through module 30, and a plurality of exterior surface electrodes 32.

The energy storage module 28 is coupled on one end to the circuit module 26 and on the other end to the feed-through module 30.

The circuit module 26 includes an interior cavity that houses a programmable memory 34, active electrical circuitry 36, and telemetry/charging coil 38. The active electrical circuitry 36 within the circuit module 26 is coupled to the electrodes 32 via a number of feed-throughs 40 in the feed-through assembly 30 and a plurality of respective electrical traces 42. Any other components of the microstimulator 12 that may best serve a particular application may also be housed within the circuit module 26.

The energy storage module 28 contains an energy storage device 44, such as a battery, is configured to output a voltage used to supply the various components within the microstimulator 12 with power. The battery 44 also provides power for any stimulation current applied by the microstimulator 12 to a stimulation site. The battery 44 may be a primary battery, a rechargeable battery, a capacitor, or any other suitable power source.

The electrodes 32 (labeled $E_1$-$E_N$) are configured to apply the electrical pulsed stimulation current to the stimulation site. As depicted in FIG. 3, there may be any number of electrodes 32 as best serves a particular application. In some examples, one or more of the electrodes 32 may be designated as stimulating electrodes and one of the electrodes 32 may be designated as an indifferent electrode used to complete one or more stimulation circuits. Any of the electrodes 32 may be configured as anodes or cathodes and the polarity of each electrode 32 may be reprogrammed. In an alternative embodiment, an electrode carrying lead (not shown) may be coupled to the microstimulator 12 in addition to or as an alternative to the electrodes 32.

The programmable memory 34 is used for storing one or more sets of data, for example, electrical stimulation parameters. The programmable memory 34 allows a patient, clinician, or other user of the microstimulator 12 to adjust the electrical stimulation parameters to levels that are safe and efficacious for a particular medical condition and/or for a particular patient. The electrical stimulation parameters may control various parameters of the stimulation current applied to the stimulation site including, but not limited to, electrode polarity, pulse amplitude, pulse rate, pulse width, burst pattern (e.g., burst on time and burst off time), duty cycle or burst repeat interval, ramp on time and ramp off time of the pulsed stimulation current that is applied to the stimulation site. The programmable memory 34 may be any type of memory unit such as, but not limited to, random access memory (RAM), static RAM (SRAM), a hard drive, or the like.

The active electrical circuitry 36 is configured for generating pulsed electrical stimulation current that is delivered to the stimulation site via the electrodes 32. The electrical circuitry 36 may be configured to produce monopolar or multipolar stimulation. The electrical circuitry 36 may include one or more processors (not shown) configured for decoding the stimulation parameter information stored in the programmable memory 34 and generating the corresponding pulsed electrical stimulation current. In some embodiments, the microstimulator 12 has at least four channels and drives up to sixteen electrodes or more. The active electrical circuitry 36 may include additional circuitry such as capacitors, integrated circuits, resistors, coils, and the like configured to perform a variety of functions as best serves a particular application.

The telemetry/charging coil 38 is configured for transcutaneously receiving data from and/or transmitting data to an external control device, such as the RC 14 or CP 16, and receiving power from the external charger 18 that is stored in the battery 40. In the illustrated embodiment, such data and power is transmitted and/or received via electromagnetic energy (also referred to as a radio frequency (RF) field).

Further details discussing microstimulators are disclosed in U.S. patent application Ser. No. 10/178,011, entitled "Implantable Microstimulators with Programmable Multi-electrode Configuration and Uses Thereof," and U.S. patent application Ser. No. 11/280,620, entitled "Implantable Stimulator," which are expressly incorporated herein by reference. In alternative embodiments, an implantable pulse generator (IPG) with one or more attached neurostimulation leads (not shown) may be used in place of the microstimulator, as disclosed in U.S. Pat. No. 6,516,227, U.S. Patent Publication No. 2003/0139781, and U.S. patent application Ser. No. 11/138,632, entitled "Low Power Loss Current Digital-to-Analog Converter Used in an Implantable Pulse Generator," which are expressly incorporated herein by reference. In this regard, the case of the IPG may be used as a relatively large cathode, and one or more electrodes on the lead(s) may be used anodes to provide a monopolar electrical field that may broaden the stimulation coverage as compared to a monopolar or bipolar electric field that can be generated by the microstimulator 12.

It should be noted that rather than a microstimulator or IPG, the neurostimulation system 10 may alternatively utilize a neurostimulator in the form of an implantable receiver-stimulator (not shown). In this case, the power source, e.g., a battery, for powering the implanted receiver, as well as control circuitry to command the receiver-stimulator, will be contained in an external controller inductively coupled to the receiver-stimulator via an electromagnetic link. Data/power signals are transcutaneously coupled from a cable-connected transmission coil placed over the implanted receiver-stimulator. The implanted receiver-stimulator receives the signal and generates the stimulation in accordance with the control signals.

Significant to the present inventions, the microstimulator 12 may be operated in a manner such that the amplitude of the electrical stimulation energy (which in the preferred method, is anodic) conveyed from the electrodes 32 may be increased in order to activate nerve endings in the far-field (e.g., the nerve endings 47a) without over-stimulating the nerve endings in the near-field (e.g., the nerve endings 47b) that may otherwise cause a painful sensation in the peripheral target region 45. In particular, the activation threshold of the near-field nerve endings 47b is increased, thereby rendering the near-field nerve endings 47b less excitable to the electrical stimulation energy. Thus, stimulation of these near-field nerve endings 47b (and possibly any painful sensation associated with this stimulation) that may otherwise result from the conveyance of the electrical stimulation energy is prevented or at least minimized.

For example, the activation threshold of the near-field nerve endings 47b may be increased by conveying electrical conditioning pulses from the electrode 36 closest to the near-field nerve endings 47b. If the electrical stimulation energy comprises a plurality of electrical stimulation pulses, the conditioning pulses may respectively precede the electrical stimulation pulses. In one method, the conditioning pulses are conventional sub-threshold depolarizing pulses that depolarize the near-field nerve endings 47b prior to exposure to the stimulation pulses. In another method, the conditioning pulses are sub-threshold hyperpolarizing pulses, each of which has a relatively short duration (e.g., less than 200 μs).

Further details discussing this technique are described in U.S. Pat. No. 7,742,810, which is expressly incorporated herein by reference.

As another example, the activation threshold of the near-field nerve endings 47b may be increased by conveying high frequency electrical blocking energy to block activation of the near-field nerve endings 47b. The high frequency electrical blocking energy may be sinusoidal and may be, e.g., in the range of 2.2 KHz-5 KHz.

In one method, the electrical stimulation energy conveyed by the electrode(s) 32 may be the same high frequency electrical blocking energy used to block activation of the near-field nerve endings 47b. In this case, the high frequency electrical blocking energy is conveyed from the electrode 32 that is closest to the near-field nerve endings 47b. Notably, the blocking threshold of a nerve fiber by high frequency electrical blocking energy is higher than the threshold at which the nerve fiber is activated by the same high frequency electrical blocking energy. Thus, if the high frequency electrical blocking energy has an amplitude that is higher than the blocking threshold the nerve endings 47, the far-field nerve endings 47a will still have a blocking threshold above the amplitude of the high frequency electrical blocking energy, but a stimulation threshold below the amplitude of the high frequency electrical blocking energy. This means that the near-field nerve endings 47b will be blocked at a stimulation current that activates the far-field nerve endings 47a. Further details discussing this technique are described in U.S. patent application Ser. No. 12/819,107, entitled "Spatially Selective Nerve Stimulation in High-Frequency Nerve Condition Block and Recruitment," which is expressly incorporated herein by reference.

In another method, the high frequency electrical blocking energy and the electrical stimulation energy may be different, and thus, may be conveyed from either the same or different electrode 32 or combination of electrodes 32. For example, the electrical stimulation energy may be conveyed from any combination of the electrodes 32 that efficiency spreads the stimulation over the entire peripheral target region 45, whereas the high frequency stimulation energy may be conveyed from the electrode 32 closest to the near-field nerve endings 47b. If the same electrode or combination of electrodes 32 is used to convey both the high frequency electrical blocking energy and the electrical stimulation energy, the conveyance of the high frequency electrical blocking energy may be ceased during a plurality of time periods, and the electrical stimulation energy, in the form of a plurality of stimulation pulses, may be conveyed only during these time periods. In this manner, the high frequency electrical blocking energy and the stimulation pulses are interleaved. The electrical stimulation pulses may be conveyed at a frequency in the range of 20-100 Hz. The energy in the stimulation pulses is preferably greater than the energy in the high frequency electrical blocking energy in order to ensure that the far-field nerve endings 47a are activated.

As still another example, the activation threshold of the near-field nerve endings 47b may be increased by conveying pulsed electrical energy from the electrode 32 that is closest to the near-field nerve endings 47b prior to conveying the electrical stimulation energy from the electrodes 32, such that the near-field nerve endings 47b accommodate to the conveyed electrical stimulation energy. The pulsed electrical energy preferably has an amplitude that is less than the electrical stimulation energy. The pulse amplitude, pulse duration, and pulse rate of the pulsed electrical energy may be, e.g., 2-4 mA, 100-500 µs, and 40-100 Hz, and can be delivered to the near-field nerve endings 47b for seconds to minutes to allow the near-field nerve endings 47b to accommodate to electrical stimulation. The electrical stimulation energy may be delivered to the nerve endings at a higher stimulation level than the pulsed electrical energy to ensure activation of the far-field nerve endings 47a.

In yet another example, the activation threshold of the near-field nerve endings 47b is performed by applying a neuronal inhibitory pharmacological agent (e.g., Na-channel blockers, Ca-channel blockers, lidocaine, etc.) to the near-field nerve endings 47b. In one embodiment, the one or more of the electrodes 32 may be coated with the neuronal inhibitory pharmacological agent. Alternatively, the microstimulator 12 may contain the neuronal inhibitory pharmacological agent, which may be slowly released from pores (not shown). The neuronal inhibitory pharmacological agent may alternatively promote fibrosis around one or more of the electrodes 32 adjacent the near-field nerve endings 47b, such that these electrodes 32 are positioned further from the near-field nerve endings 47b via benign fibrotic tissue. Alternatively, the neuronal inhibitory pharmacological agent may promote angiogenesis to allow for spread of the electrical current to further distances via vascular pathways.

In yet another example, the activation threshold of the near-field nerve endings 47b is performed by ablating the near-field nerve endings 47b. In one method, radio frequency (RF) energy may be delivered to ablate the near-field nerve endings 47b prior to implantation of the microstimulator 12 in order to "stun" or damage the near-field nerve endings 47b, such that they are difficult or impossible to activate with electrical stimulation energy. Alternatively, the ablative energy may take the form of laser, direct thermal, pharmacological, and mechanical/surgical techniques.

Although particular embodiments of the present inventions have been shown and described, it will be understood that it is not intended to limit the present inventions to the preferred embodiments, and it will be obvious to those skilled in the art that various changes and modifications may be made without departing from the spirit and scope of the present inventions. Thus, the present inventions are intended to cover alternatives, modifications, and equivalents, which may be included within the spirit and scope of the present inventions as defined by the claims.

What is claimed is:

1. A method of providing therapy to a patient having a disorder using a receiver-stimulator implanted within a patient, an external controller inductively coupled to the receiver-stimulator via an electromagnetic link, and an electrode coupled to the receiver-stimulator and located adjacent a peripheral target neural region of the patient, the method comprising:

transcutaneously transmitting data/power signals from the external controller to the receiver-stimulator via the electromagnetic link; and in response to the transmitted data/power signals, conveying electrical stimulation energy from the electrode that stimulates a first set of nerve endings in the peripheral target neural region, the first set of nerve endings being relatively far from the electrode, and increasing an activation threshold of a second set of nerve endings in the peripheral target neural region, thereby rendering the second set of nerve endings less excitable to the electrical stimulation energy, the second set of nerve endings being relatively near the electrode.

2. The method of claim 1, wherein the electrical stimulation energy is conveyed in a monopolar manner.

3. The method of claim 1, wherein the electrical stimulation energy is conveyed in a multipolar manner.

4. The method of claim 1, wherein increasing the activation threshold of the second set of nerve endings results in preventing stimulation of the second set of nerve endings.

5. The method of claim 1, wherein conveying the electrical stimulation energy comprises conveying at least one stimulation pulse, and wherein increasing the activation threshold of the second set of nerve endings is performed by conveying at least one electrical conditioning pulse to the second set of nerve endings.

6. The method of claim 5, wherein each of the at least one conditioning pulse is a depolarizing conditioning pulse.

7. The method of claim 5, wherein each of the at least one conditioning pulse is a hyperpolarizing conditioning pulse have a duration of less than 200 μs).

8. The method of claim 5, wherein the at least one conditioning pulse is conveyed from the electrode.

9. The method of claim 5, wherein the at least one conditioning pulse respectively precede the at least one stimulation pulse.

10. The method of claim 1, wherein increasing the activation threshold of the second set of nerve endings is performed by conveying high frequency electrical blocking energy to the second set of nerve endings.

11. The method of claim 10, wherein the high frequency electrical blocking energy is at least 2.2 kHz.

12. The method of claim 10, wherein the high frequency electrical blocking energy is sinusoidal.

13. The method of claim 10, wherein the high frequency electrical blocking energy is the electrical stimulation energy conveyed from the electrode.

14. The method of claim 10, wherein the conveyance of the high frequency electrical blocking energy is ceased during a plurality of periods, wherein conveying the electrical stimulation energy comprises respectively conveying a plurality of stimulation pulses only during the plurality of periods.

15. The method of claim 14, wherein high frequency electrical blocking energy is at least 2.2 KHz, the plurality of stimulation pulses are conveyed at a frequency in the range of 20-100 Hz, and the energy in the plurality of stimulation pulses is greater than the high frequency electrical blocking energy.

16. The method of claim 1, wherein increasing the activation threshold of the second set of nerve endings is performed by conveying pulsed electrical energy prior to conveying the electrical stimulation energy, such that the second set of nerve endings accommodates to the conveyed electrical stimulation energy, wherein the pulsed electrical energy has an amplitude that is less than the electrical stimulation energy.

17. The method of claim 1, wherein increasing the activation threshold of the second set of nerve endings is performed by applying a neuronal inhibitory pharmacological agent to the second set of nerve endings prior to conveying the electrical stimulation energy from the electrode.

18. The method of claim 1, wherein increasing the activation threshold of the second set of nerve endings is performed by ablating the second set of nerve endings.

19. The method of claim 1, wherein the therapy is a reduction in or elimination of pain.

* * * * *